United States Patent [19]

Batchelor

[11] 4,432,969

[45] Feb. 21, 1984

[54] PHARMACEUTICAL COMPOSITIONS

[75] Inventor: Frank R. Batchelor, Surrey, England

[73] Assignee: Beecham Group P.L.C., England

[21] Appl. No.: 345,534

[22] Filed: Feb. 3, 1982

[30] Foreign Application Priority Data

Feb. 6, 1981 [GB] United Kingdom ................. 8103778

[51] Int. Cl.$^3$ .............................................. A61K 39/36

[52] U.S. Cl. ....................................... 424/91; 424/88; 424/182; 536/5

[58] Field of Search ................ 424/88, 91, 182; 536/5

[56] References Cited

U.S. PATENT DOCUMENTS

| | | | |
|---|---|---|---|
| 3,639,577 | 2/1972 | Urton et al. | 424/91 |
| 3,761,585 | 9/1973 | Mullan et al. | 424/91 |
| 3,869,546 | 3/1975 | Lund | 424/91 |
| 4,189,471 | 2/1980 | Ponpipom et al. | 424/88 |
| 4,310,550 | 1/1982 | Wolff et al. | 424/88 |

OTHER PUBLICATIONS

*Chemical Abstracts,* vol. 72, (1970), p. 198, Abstract No. 88326, Petermann et al.

*Primary Examiner*—Esther M. Kepplinger
*Assistant Examiner*—Frederick W. Pepper
*Attorney, Agent, or Firm*—Jacobs & Jacbos

[57] ABSTRACT

An inhalent allergen composition comprises an inhalent allergen and a saponin adjuvant. The inhalent allergen may be an extract of a grass pollen, such as rye grass, or a weed, such as ragweed. The saponin adjuvant may be an extract from the bark of the tree Quillaja Molina, and known as Quil-A.

10 Claims, No Drawings

PHARMACEUTICAL COMPOSITIONS

This invention relates to pharmaceutical compositions, their use in the therapy of allergic humans, and to a process for their preparation.

Saponin adjuvants are a known class of adjuvants which have been used commercially to adjuvant Foot and Mouth Disease vaccines for animals.

It has now surprisingly been found that such adjuvants are useful in inhalent allergen compositions, which compositions may be used in the desensitisation therapy of humans allergic to inhalent allergens.

Accordingly the present invention provides a pharmaceutical composition, which composition comprises an inhalent allergen and a saponin adjuvant optionally in combination with a pharmaceutically acceptable carrier.

The adjuvant is suitably in the form of a physical admixture with the allergen in the composition of the invention, although under certain conditions some degree of conjugation or covalent bonding between the adjuvant and the allergen can occur.

Such conjugation suitably occurs by first preparing a modified form of the adjuvant in which the functional groups of the adjuvant are activated, and linking this activated form to the allergen. Suitable activating agents for the adjuvant are carboxyl activating agents well known to those skilled in the art. A particularly useful activating agent is N-(3-dimethylaminopropyl)-$N^1$-ethyl carbodiimide (CDI), which may be used in combination with N-hydroxysuccinimide.

Both physical admixture and conjugation of the active ingredients are within the scope of the compositions of the invention.

The inhalent allergen for use in this invention is suitably in the form of an extract of whole allergen. Suitable whole allergens from which the extract can be obtained may be chosen from any allergen which exerts its effect via inhalation. By way of illustration pollens, such as grass pollens, for example rye; weeds, such as ragweed; house dust mites; and dander; are all suitable. These extracts of allergen are water soluble. More suitably the allergen is an extract of a grass pollen.

The extraction of the allergenic material may be carried out by treating the whole allergen with a suitable solvent, usually aqueous. The allergenic extract may then be purified by removing contaminants e.g. by dialysis, precipitation or gel filtration. In another useful extraction procedure, the whole allergen or an aqueous extract thereof, is treated with aqueous phenol and the allergenic extract is recovered from the phenol phase.

It will of course be appreciated that it is well known in the art that such allergens may be modified prior to use to achieve an optimisation of properties. By way of example, a glutaraldehyde modified allergen may be used, such materials being described fully in U.K. Pat. No. 1,282,163.

Also of course other known formulation techniques may be used with the allergens for use in this invention—they may for example be adsorbed (modified or unmodified) onto tyrosine, as fully described in U.K. Pat. Nos. 1,377,074 and 1,492,973.

As noted above, saponin adjuvants are a known class of adjuvants readily recognisable to the skilled man. These adjuvants have been used extensively for at least twenty years without any suggestion that they might be useful in the particular manner referred to herein, namely to potentiate the antibody response to inhalent allergens.

The saponin adjuvants are natural products widely distributed in, for example, plant families. They are generally characterised by a number of common properties, such as the ability to foam in aqueous solution, hemolytic activity, toxicity for fish, and complexing with cholesterol. Their chemical structures are, in many cases, not fully elucidated, but saponins can be characterised by having a steroid or triterpenoid moiety attached to a carbohydrate moiety (see for example Acta Vet Scan Supp 69, 1–40 (1978)).

It will be appreciated that, as is normally the case when administration to humans is being considered, the purity of the materials administered is important. One commercially available saponin adjuvant of good purity is that well known by the name Quil-A, which is available from Superfos a/s, Frydenlundsvej 30, DK-2950 Vedbaek, Denmark. The physical and chemical characteristics of Quil-A are conveniently set out in the trade literature available from Superfos, entitled Purified Saponin Adjuvant Quil-A. It is noted in particular that Quil-A may be isolated from the bark of the South American tree Quillaja Saponaria Molina, and is characterised chemically as a carbohydrate moiety in glycosidic linkage to the triterpenoid quillaic acid.

From the aforesaid it will be appreciated that a preferred composition of this invention comprises an inhalent allergen and Quil-A.

In such preferred compositions, often the inhalent allergen will be a grass pollen such as rye.

The quantities of allergen used in the pharmaceutical compositions of the invention will be as conventional for that allergen in desensitisation therapy. By way of example the composition might suitably contain 0.1 to 10,000 pnu of allergen, the lower end of this range being more appropriate for early in the therapy, the higher end of this range being more appropriate for later in the therapy.

The quantities of Quil-A that can be used in the pharmaceutical compositions of this invention are limited really only in that too high levels might begin to show toxic effects, and too low levels will obviously not exert a meaningful adjuvant effect.

Within these boundaries, it is believed that it is a routine matter to derive a suitable level for the particular saponin and the particular allergen, to obtain the desired adjuvant effect coupled with pharmaceutical safety. By way of example, suitable levels of saponin adjuvant might be in the range 5 to 100, more suitably 25 to 75, for example 50 μg per injection.

The pharmaceutical compositions of this invention may be used as vaccines in the desensitisation of humans allergic to inhalent allergens. Thus the compositions will suitably be in the form of solutions or suspensions, in a liquid vehicle. Preferably the compositions will be aqueous solutions or suspensions.

Usually a patient receiving treatment with such a composition is administered a number of injections, spread over a period of weeks or days.

The invention also provides a process for the preparation of the compositions of this invention, which process comprises bringing into conjunction the allergen and the saponin adjuvant.

This process is conveniently carried out merely by mixing together the allergen and the saponin adjuvant in the presence of a suitable inert solvent, preferably water.

In a further aspect of the process of the invention, the allergen is covalently bonded to the saponin adjuvant by, for example, preparing an activated form of the adjuvant, as hereinbefore described, and mixing this with the allergen.

It will of course be appreciated that the compositions of this invention may suitably contain as additional ingredients any of the conventional vaccine additives, such as sodium chloride, phosphates and preservatives.

The invention also provides a method of treating humans allergic to inhalent allergens, which method comprises administering to the sufferer an effective amount of a composition according to this invention.

The following Examples illustrate the invention.

EXAMPLE I

Preparation of Injectable Rye/Quil-A Compositions

A: Rye/Quil-A

Rye grass pollen extract (R.E.) (1 mg) was dissolved in phosphate buffered saline (Bacto Haemagglutination buffer from Difco) (1 ml) containing Quil-A (50 μg).

B: Rye/Tyrosine

R.E. (1 mg) was adsorbed to L-tyrosine (40 mg) in phosphate buffered phenol saline (1 ml).

The absorbate was prepared as follows:
Solution
(1) 24% w/v L-tyrosine in 3.8 M. HCl;
(2) 3.2 N. NaOH;
(3) $Na_2HPO_4$ (11.8 g)+$NaH_2PO_4.2H_2O$ (3.0 g) made up to 100 ml with water;
(4) Phosphate buffered saline (Difco);
(5) Phenol (5 g), NaCl (8 g), $Na_2HPO_4$ (0.2 g), $NaH_2PO_4.2H_2O$ (1.5 g), made up to 1 liter with water and the pH adjusted to 7.0 with NaOH+HCl;
(6) R.E. was made up at twice the final required concentration in 30 ml of solution (4).

10 ml of solution (3) was added to solution (6), then solution (1) (10 ml) and solution (2) (10 ml) were run into this at approximately 1 ml/minute using peristaltic pumps whilst stirring vigorously. The pH was not allowed to vary more than 0.5 pH units.

The resulting precipitate was centrifuged for 10 minutes and washed twice with solution (5) and resuspended with 60 ml of solution (5).

C: Rye/Tyrosine/Quil-A

To 1 ml of the B preparation was added 50 μg of Quil-A in a minimal volume.

D: Rye

R.E. (1 mg) was dissolved in phosphate buffered saline (1 ml).

N.B. The Quil-A referred to above was obtained from Superfos a/s as a sterile aqueous solution containing 1.5% Quil-A dry matter. Difco's address is Detroit, Mich., USA.

Immunisation Schedule

Four groups of six female mature Hartley Strain Guinea Pigs received 1 ml sub-cutaneous injections of preparations A, B, C or D respectively. They were then each given a further sub-cutaneous injection of 1 ml of phosphate buffered saline containing 100 μg of R.E. on day 28. The animals were bled on days 23 and 35 and sera prepared.

The sera were tested for the presence of R.E. specific haemagglutinating antibody by the standard method of 'Chemical Modification of Crude Timothy Grass Pollen Extract. Antigenicity and Immunogenicity changes following amino group modification—D M Moran and A W Wheeler, Int Archs Allergy appl Immun 50: 693–708 (1976)'.

| Guinea Pig Number | Immunogen Preparation | Haemagglutination Titre $-\log_2$ from ½, on day 23 | 35 |
|---|---|---|---|
| A1 | A | 8 | 13 |
| A2 |   | 7 | 13 |
| A3 |   | 7 | 11 |
| A4 |   | 7 | 11 |
| A5 |   | 6 | 10 |
| A6 |   | 5 | 14 |
| B1 | B | <1 | Died |
| B2 |   | <1 | Died |
| B3 |   | <1 | 9 |
| B4 |   | <1 | Died |
| B5 |   | <1 | 9 |
| B6 |   | 4 | 9 |
| C1 | C | 7 | 12 |
| C2 |   | 7 | 11 |
| C3 |   | 8 | 12 |
| C4 |   | 6 | 13 |
| C5 |   | 7 | Died |
| C6 |   | 8 | 11 |
| D1 | D | <1 | 8 |
| D2 |   | <1 | 6 |
| D3 |   | <1 | 7 |
| D4 |   | <1 | <1 |
| D5 |   | <1 | 7 |
| D6 |   | <1 | Died |

Conclusion

The effectiveness of Quil-A as an adjuvant is shown in these tests.

EXAMPLE 2

Preparation of Quil-A-Rye Conjugate Composition

Samples of Quil-A (amounts shown in Table 1 below) were dissolved in N,N-dimethylformamide (DMF) (1 ml) and N-hydroxysuccinimide (HOSu) (2 equiv.) added. The solution was cooled in ice-water before the addition of N-(3-dimethylaminopropyl)-$N^1$-ethylcarbodiimide hydrochloride (CDI) (1 equiv.) in DMF (0.5 ml). After stirring for 15 mins at 4° C. and 30 mins while warming to room temperature these solutions were added to solutions of rye grass pollen extract (R.E.) (25 mg) in sodium borate buffer (0.1 m, pH 8.5) (5 ml) cooled in ice-water. The mixtures were stirred at 4° C. for 15 mins then at room temperature for 3 hours and at 5° C. for for 20 hours. The solutions were then dialysed against 10 mM ammonium bicarbonate (3×4 l) and lyophilised. The residual materials were characterised by primary amino group (1° $NH_2$) analysis and a Radioallergosorbent inhibition test (RAST inhibition).

TABLE 1

| Sample No. | Amounts of reagents used/mg Quil-A | CDI | HOS u | Yield/mg | 1° $NH_2$ gps. μmole/mg | RAST redn. (n fold) |
|---|---|---|---|---|---|---|
| 1 | 0 | 0 | 0 | 16 | 0.76 | 0 |
| 2 | 5 | 0.43 | 0.5 | 15 | 0.72 | 7 |
| 3 | 10 | 0.85 | 1.0 | 27 | 0.69 | 23 |
| 4 | 30 | 2.55 | 3.0 | 23 | 0.52 | 108 |

Haemagglutinating antibody induction in guinea pigs with Quil-A-Rye

Groups of six guinea pigs were immunised with 1 mg of sample in PBS (Difco bacto-haemagglutination buffer) given in two subcutaneous sites; and were boosted similarly on day 28 with 100 μg of sample.

| Group | Sample No. | Immunogen |
|---|---|---|
| A | 1 | Native rye extract |
| B | 1 | Buffer control rye extract |
| C | 2 | Quil-A-rye |
| D | 3 | Quil-A-rye |
| E | 4 | Quil-A-rye |

Antibody to rye grass pollen extract was measured by the haemagglutination method described in Example 1 and the results are shown in Table 2. It is apparent from the results that conjugation of the Quil A to the rye grass pollen extract increased the propensity of this antigen to produce rye grass pollen specific haemagglutinating antibody.

TABLE 2

| | | Rye specific IgG by haemagglutination $-\log_2$ from ½, on day | | |
|---|---|---|---|---|
| Group | g. pig | 14 Titre | 28 Titre | 35 Titre |
| Native rye extract | A1 | 5 | 3 | 6 |
| | 2 | 4 | 3 | 9 |
| | 3 | 4 | 4 | 9 |
| | 4 | 6 | 6 | 8 |
| | 5 | 0 | 5 | 10 |
| | 6 | 0 | 5 | >12 |
| | Av. | 3.2 | 4.3 | >9 |
| Buffer control rye extract Sample 1 | B1 | 6 | 6 | 10 |
| | 2 | 2 | 5 | 9 |
| | 3 | 3 | 4 | 7 |
| | 4 | 4 | 5 | 9 |
| | 5 | 3 | 0 | 7 |
| | 6 | 5 | 4 | 8 |
| | Av. | 3.8 | 4 | 8.3 |
| Sample 2 | C1 | 8 | 7 | 11 |
| | 2 | 9 | 3 | 10 |
| | 3 | 0 | 7 | 11 |
| | 4 | 7 | 7 | 9 |
| | 5 | 0 | 4 | 7 |
| | 6 | 9 | 6 | >12 |
| | Av. | 5.5 | 5.7 | >10 |
| Sample 3 | D1 | 7 | 5 | >12 |
| | 2 | 7 | 8 | >12 |
| | 3 | 0 | 5 | 11 |
| | 4 | 0 | 5 | 9 |
| | 5 | 0 | 7 | 12 |
| | 6 | 9 | 8 | 11 |
| | Av. | 3.8 | 6.3 | >11.2 |
| Sample 4 | E1 | 6 | 6 | 12 |
| | 2 | 6 | 5 | 7 |
| | 3 | 9 | 10 | >12 |
| | 4 | 8 | 9 | >12 |
| | 5 | 7 | 8 | 12 |
| | 6 | 12 | 12 | 12 |
| | Av. | 8 | 8.3 | >11.2 |

I claim:

1. An anti-allergenic pharmaceutical composition comprising a desensitizing effective amount of an inhalent allergen and an adjuvant effective amount of a saponin adjuvant, in combination with a pharmaceutically acceptable carrier.

2. A composition according to claim 1, in which the allergen comprises an extract of a grass pollen or a weed.

3. A composition according to claim 1, in which the allergen is modified with glutaraldehyde and/or adsorbed onto tyrosine.

4. A composition according to claim 1, in which the saponin adjuvant comprises Quil-A.

5. A composition according to claim 1, in which the composition contains from 0.1 to 10,000 pnu of allergen.

6. A composition according to claim 1, in the form of a solution or suspension in a pharmaceutically acceptable liquid vehicle.

7. A composition according to claim 6 suitable for use as a vaccine.

8. A composition according to claim 7, in which the concentration of saponin adjuvant is selected to provide from 5 to 100 μg of adjuvant per injection.

9. A composition according to claim 1, comprising rye grass pollen extract and Quil-A.

10. A method of treating humans allergic to inhalent allergens, which comprises administering to the sufferer an amount effective for desensitization to said allergen of a composition according to claim 1.

* * * * *